United States Patent [19]

Mashkovsky et al.

[11] 4,117,139

[45] Sep. 26, 1978

[54] MEDICATED COMPOUND FOR TREATING ALLERGIC DISEASES

[76] Inventors: Mikhail Davydovich Mashkovsky, Leningradsky prospekt, 75a, kv. 55; Leonid Nikolaevich Yakhontov, Nakhimovsky prospekt, 1, korpus 1, kv. 22; Andrei Dmitrievich Ado, Kotelnicheskaya naberezhnava, 1/15, kv. 295; Mikhail Emmanuilovich Kaminka, ulitsa Lobachevskogo, 12, kv. 29; Eva Evseevna Mikhlina, Kutuzovsky prospekt, 5/3, korpus 2, kv. 151; Valentina Yakovlevna Vorobieva, Novo-Alexeevskaya ulitsa, 5a, kv. 13; Anna Dmitrievna Yanina, Karachinovsky proezd, 22, kv. 132.; Nadezhda Andreevna Komarova, ulitsa Shabolovka, 65, korpus 2, kv. 86, all of Moscow, U.S.S.R.

[21] Appl. No.: 752,127

[22] Filed: Dec. 20, 1976

Related U.S. Application Data

[63] Continuation of Ser. No. 525,633, Nov. 20, 1974, abandoned.

[30] Foreign Application Priority Data

Dec. 18, 1973 [SU] U.S.S.R. ............... 1979715

[51] Int. Cl.$^2$ .................................... A61K 31/445
[52] U.S. Cl. ............................................. 424/267
[58] Field of Search ................................. 424/267

[56] References Cited

PUBLICATIONS

Chem. Abst., vol. 65, 12163 (1966).

*Primary Examiner*—Stanley J. Friedman
*Attorney, Agent, or Firm*—Holman & Stern

[57] ABSTRACT

A medicated compound for treating allergic diseases which consists of an active principle, viz. (quinuclidyl-3)-diphenylcarbinol hydrochloride of the formula:

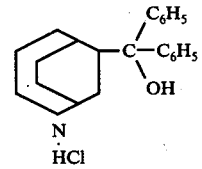

in combination with a pharmaceutical filler or a solvent for injection solutions.

8 Claims, No Drawings

MEDICATED COMPOUND FOR TREATING ALLERGIC DISEASES

This is a continuation of application Ser. No. 525,633, filed Nov. 20, 1974, now abandoned.

The present invention relates to a novel medicated compound for treating allergic diseases.

In accordance with the present invention, a medicated compound for treating allergic diseases consists of an active principle, viz. (quinuclidyl-3)-diphenylcarbinol hydrochloride of the formula:

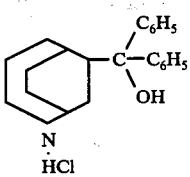

in combination with a pharmaceutical filler or solvent for injection solutions.

The medicated compound of the present invention is useful in the medical practice for treating allergic responses in pathogenesis wherein histamine activity has an important role, namely in pollinosis, urticaria, Quincke's oedema, serum disease, vasomotor rhimitis, itching dermatosis, food allergia, allergic responses resulting from the administration of various medicated compounds including antibiotics.

As to the mechanism of its action, the medicated compound of the present invention represents an antagonist to histamine liberated in antigen-antibody reactions. In an experiment on narcotized guinea pigs (according to the Concette-Rossler method, 1940), the medicated compound of the present invention when administered intravenously in a dose from 0.1 to 0.2 mg/kg weakens, or inhibits the bronchoconstricting action of histamine. In these experiments the medicated compound of the present invention is by from 1.5 to 2 times as efficient as dimedrol (diphenhydramine hydrochloride) in the activity and duration of action thereof.

The medicated compound of the present invention exerts only a slight influence on bronchospasm caused by serotonine (5-hydroxytriptamine) or acetylcholine.

The medicated compound of the present invention when administered intravenously to narcotized cats in doses of from 0.2 to 0.5 mg/kg prevents hypotensive activity of intravenously injected histamine (1 mcg/kg).

The medicated compound of the present invention, when administered in the stomach in doses of from 30 to 50 mg/kg to narcotized guinea pigs, completely protects the animals for from to 2 to 3 hours from intoxication (disp nea, apnoea, clono-tonic spasm) caused by an aerosol of a 1.5% solution of 1.5% histamine under continuous spraying for 300 seconds. Dimedrol, when administered under the same test conditions, in the same doses, and 1 hour after the administration merely, prolongs a latent period of intoxication from 55 (52-58) seconds in the control animals to 173 (264-82) seconds in the test group (at $p$ of at least 0.05). In these experiments dimedrol protects the animals for from 4 to 5 hours from death caused by histamine aerosol, whereas the action of the medicated compound of the present invention lasts for from 10 to 12 hours.

The medicated compound of the present invention when administered into the stomach in a dose of 50 mg/kg prevents or substantially reduces ophthalmic response (hyperemia and chemosis) with guinea pigs caused by instillation of a 2% solution of histamine into a conjunctival sac.

The effect of dimedrol in similar experiments is much less pronounced and lasts for 8 to 10 hours.

The medicated compound of the present invention when administered to guinea pigs, actively sensibilized with ovalbumin in doses of 25 mg/kg intraperitoneally, and 50 mg/kg in stomach respectively causes a clearly pronounced antiallergic effect increasing the latent period, or completely inhibiting signs of anaphylactic response (breathing in intermittence, clono-tonic spasms) caused by aerosol treatment of the animals with a 25% solution of ovalbumin for 10 minutes.

The medicated compound of the present invention irrespectively of the medication mode exerts antiedemic antianaphylactic action. The medicated compound of the present invention when administered intraperitoneally to non-narcotized rats in the dose of 25 mg/kg and in the stomach in the dose of 50 mg/kg (at $P$ over 0.05) actually reduces, by more than 2 times, foot edema of hind limb caused by a subplantar medication of serotonin (5 mcg calculated on the base), formalin, (0.2 ml of a 2% solution), dextrane (0.1 ml of a 6% solution). In respect of these characteristics the medicated compound of the present invention is more efficient than dimedrol, and more active than diprasine (promethasine).

The medicated compound of the present invention when administered hypodermically in a dose of 25 mg/kg exerts a pronounced anti-inflammation effect in the case of a chronic aseptic inflammation caused by hypodermical implantation of wool balls to rats; in respect to this characteristic, it is also superior over dimedrol.

Detailed pharmacological and toxicological studies of the medicated compound of the present invention have shown that this medicated compound exerts only a relatively slight influence on the heart-vascular system, digestive tract, and excretory organs.

An important feature of the medicated compound of the present invention resides in that it does not exert a depressive effect on the central nervous system. The majority of modern anti-histamine medicines reveal a strong sedative effect, whereby their administration is substantially limited in the ambulatory treatment, especially in the case of persons engaged in intellectual pursuits, or persons whose occupation requires quick physical and psychic responses, e.g. drivers of transport vehicles.

The medicated compound of the present invention, in the experiments on various test animals (mice, rats, rabbits, cats) and with different modes of administration, excerts no influence on spontaneous motor activity, summation ability of the central nervous system; it further does not extend the action of various hypnotics, nor has it any influence on an electroencephalogram or the latent period of conditioned reflexes.

At a single medication (by different modes) to mice, rats, guinea pigs, cats and dogs, the medicated compound of the present invention influences the general state and behaviour of animals to a considerably lesser extent than dimedrol (diphenhydramine) and especially diprasine (promethasine).

The medicated compound of the present invention exhibits relatively low-toxicity its average lethal dose ($LD_{50}$) for mice at a single intravenous medication is 62 mg/kg, in the stomach 370 mg/kg, whereas the $LD_{50}$ of dimedrol is 39 and 210 mg/kg respectively, and doses of diprasine (promethasine) results in the death of half of the animals when 25 mg/kg are administered intravenously.

$LD_{50}$ of the medicated compound of the present invention administered in the stomach to rats is 440 mg/kg; the absolute lethal dose of the medicated compound administered to guinea pigs is 500 mg/kg.

Repeated administration of the medicated compound of the present invention in relatively high doses is well tolerated by the test animals. Thus, when administered to rats (in the stomach) for 22 times in the doses equalling ¼ of $LD_{50}$, the medicated compound of the present invention has no essential influence on the general state and behaviour of the animals, the pattern of peripheral blood, the biochemical characteristics of blood and the urina. Under said experimental conditions, the medicated compound of the present invention results in no pathomorphological changes in internal organs.

The medicated compound of the present invention when administered per os to rats in single doses equalling ¾ of $LD_{50}$ in various periods of pregnancy does not exert any embriotoxic or teratogenic effects.

The medicated compound of the present invention was clinically tested on 250 patients aging from 18 to 70 years suffering from allergic diseases for a period of from 3 months to 10 years, and treated with various anti-histamine medicines.

The treatment with the medicated compound of the present invention was effected in allergological surgeries under ambulatory and stationary conditions.

The majority of the stationary patients were hospitalized with serious, or lasting allergic responses and frequently with accompanying diseases of the heart-vascular system, and digestive tract.

The medicated compound of the present invention was used for the treatment of acute and chronic urticaria, hay fever, Quincke's oedema, dermal itch, chronic eczema, polysyndromic phenomena of intolerance (arthropathy, eosinophilia, temperature increase), dermatoblepharoconjunctivitis, and bronchial-asthma.

The medicated compound of the present invention has been inefficient in the treatment of bronchial asthma.

In the case of dermatoblepharonconjunctivitis and some other allergic ophthalmic diseases, the medicated compound of the present invention was administered per os (one tablet of 0.025 g 3 to 4 times per day). The medicated compound revealed a satisfactory curing action. Its therapeutic effect was enhanced and the treatment course was shortened (from 18 to 20 days from 12 to 15 days) in the case of a simultaneous administration of corticosteroids (dexamethazone).

The medicated compound of the present invention was highly efficient in the case of acute and chronic urticaria, hay fever, vasomotor rhinitis, Quincke's oedema, itching dermatosis, chronic eczema, and polysyndromic phenomena of intolerance.

Said diseases were caused by the following allergens: plant pollen, home dust, food products, synthetic medicines, antibiotics, and whey protein.

The medicated compound of the present invention was used individually (without an additional desensibilizing therapy) per os in a dose of from 3 to 6 tablets (0.025 g each) per day, usually directed after eating.

After only 3 days from the beginning of said treatment the condition of patients was better, with dermal eruptions and itching being reduced.

Considerable improvement of the general condition was noticed at from 65 to 85% of convalescent patients after the medicated compound was administered for from 12 to 18 days.

It has also been found that the medicated compound of the present invention is efficient in patients with a developed adaptation to other anti-histamine medicines.

In accordance with the present invention, the medicated compound consists of an active principle, viz. (Quinuclidyl-3)-diphenylcarbinol hydrochloride in combination with a pharmaceutical filler, solvent and injection solutions. As the filler preferably used is starch or sugar powder. The active principle content in one tablet ranges from 0.01 to 0.05 g.

As the pharmaceutical solvent for injection solutions it is advisable to use propylene glycol. The active principle content in an injection solution is from 1 to 2 wt.%.

The active principle (quinuclidyl-3)-diphenylcarbinol hydrochloride is preferably prepared in the manner as follows:

Quinuclidyl-3-carboxylic acid ethylate is dissolved in an organic solvent such as diethyl ether. Then, upon cooling to from −5° to +10° C, it is reacted with arylor heteryl metals (such as phenyl lithium, phenyl magnesium bromide). The mixture is maintained at room temperature for 20 hours, cooled from 0° to +10° C whereupon the (quinuclidyl-3)-diphenyl carbinol is isolated which is then converted to (quinucleidyl-3)-diphenylcarbinol hydrochloride by treatment with an alcoholic solution of hydrogen chloride.

The medicated compound of the present invention is well tolerated by, and does not exert a depressive effect on the central nervous system.

However, with the patients over 60 years of age, or those weakened by accompanying serious diseases, some cases of a "seductive" effect of the medicated compound of the present invention were noticed.

In cases where patients with accompanying serious diseases of the digestive tract (gastritis, cholecystitis, colitis) short-time phenomena of discomfort are possible which quickly disappear by themselves (in 1–2 days) without cancelling or reducing the dosage of the medicated compound.

Care should be taken in the administration of the medicated compound of the present invention to patients suffering from accompanying heart-vascular diseases (hypertensive disease, coronary insufficiency) or serious kidney troubles.

The medicated compound of the present invention must be stored in a cool and light-protected place.

What is claimed is:

1. A method of alleviating histamine-induced symptoms in a patient in need thereof which comprises administering to said patient an antihistiminically effective amount of the active principle (quinuclidyl-3)-diphenylcarbinol hydrochloride of the formula:

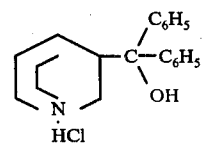

2. The method in accordance with claim 1, wherein said active principle is administered orally in the form of a tablet containing said active principle in combination with a pharmaceutical filler.

3. The method in accordance with claim 2, wherein said pharmaceutical filler is selected from the group consisting of starch and sugar powder.

4. The method in accordance with claim 2, wherein said active principle is employed in an amount of from 0.01 to 0.05 g per one tablet.

5. The method in accordance with claim 4, wherein said active principle is employed in an amount of 0.025 g per one tablet, and is administered in a dose of from 3 to 6 tablets per day.

6. The method in accordance with claim 1, wherein said active principle is administered by injection in the form of an injection solution containing said active principle in combination with a pharmaceutical solvent.

7. The method in accordance with claim 6, wherein said pharmaceutical solvent is propylene glycol.

8. The method in accordance with claim 6, wherein said active principle is employed in an amount of from 1 to 2% by weight of said injection solution.

* * * * *